United States Patent [19]

Grim et al.

[11] Patent Number: 5,348,530
[45] Date of Patent: Sep. 20, 1994

[54] PNEUMATIC ANKLE BRACE WITH BLADDER AND PUMP ARRANGEMENT

[75] Inventors: Tracy E. Grim, Broken Arrow, Okla.; William K. Arnold, Longmeadow, Mass.; Joseph M. Iglesias, Agoura, Calif.

[73] Assignee: Royce Medical Company, Camarillo, Calif.

[21] Appl. No.: 99,190

[22] Filed: Jul. 29, 1993

[51] Int. Cl.⁵ .............................................. A61F 5/00
[52] U.S. Cl. ........................................ 602/13; 602/12; 602/5
[58] Field of Search ................. 602/5, 6, 12, 13, 23, 602/27, 28, 24; 604/26, 28, 29, 32

[56] References Cited

U.S. PATENT DOCUMENTS

| | | | |
|---|---|---|---|
| 2,531,074 | 11/1950 | Miller | 604/13 X |
| 2,552,711 | 5/1951 | Dunker | |
| 2,560,591 | 7/1951 | Oltrogge | |
| 2,676,422 | 4/1954 | Crawford | |
| 3,029,530 | 7/1961 | Eaton | |
| 3,331,146 | 5/1966 | Karras | |
| 4,280,489 | 7/1981 | Johnson, Jr. | |
| 4,414,760 | 11/1983 | Faiella | |
| 4,628,945 | 12/1986 | Johnson, Jr. | |
| 4,805,601 | 2/1989 | Eischen, Sr. | 602/27 X |
| 4,844,094 | 7/1989 | Grim | 602/27 |
| 4,913,755 | 4/1990 | Grim | 602/27 X |
| 4,964,902 | 10/1990 | Grim et al. | 602/27 X |
| 4,977,891 | 12/1990 | Grim | |
| 5,125,400 | 6/1992 | Johnson, Jr. | 602/27 X |
| 5,139,475 | 8/1992 | Robicser | 602/13 X |

OTHER PUBLICATIONS

German Publication Designated Offenlegungsschrift No. 2321817, Published Nov. 15, 1973.

*Primary Examiner*—Robert A. Hafer
*Assistant Examiner*—Sam Rimell
*Attorney, Agent, or Firm*—Poms, Smith, Lande & Rose

[57] ABSTRACT

A pneumatic ankle brace having a pair of relatively rigid side supports with inflatable main bladders attached to their inside surfaces. The inflatable main bladders are coupled to an interconnected foot pump. Additional support and back-up bladders may be placed distally upon the main bladders to provide further cushioning and support. The foot pump is activated through normal use, such as walking or running, whereby entrapped fluid is displaced back and forth between the main bladders and the pump. This creates a pulsing action which provides a massaging compression effect which helps reduce swelling and increase venous and lymphatic return.

18 Claims, 3 Drawing Sheets

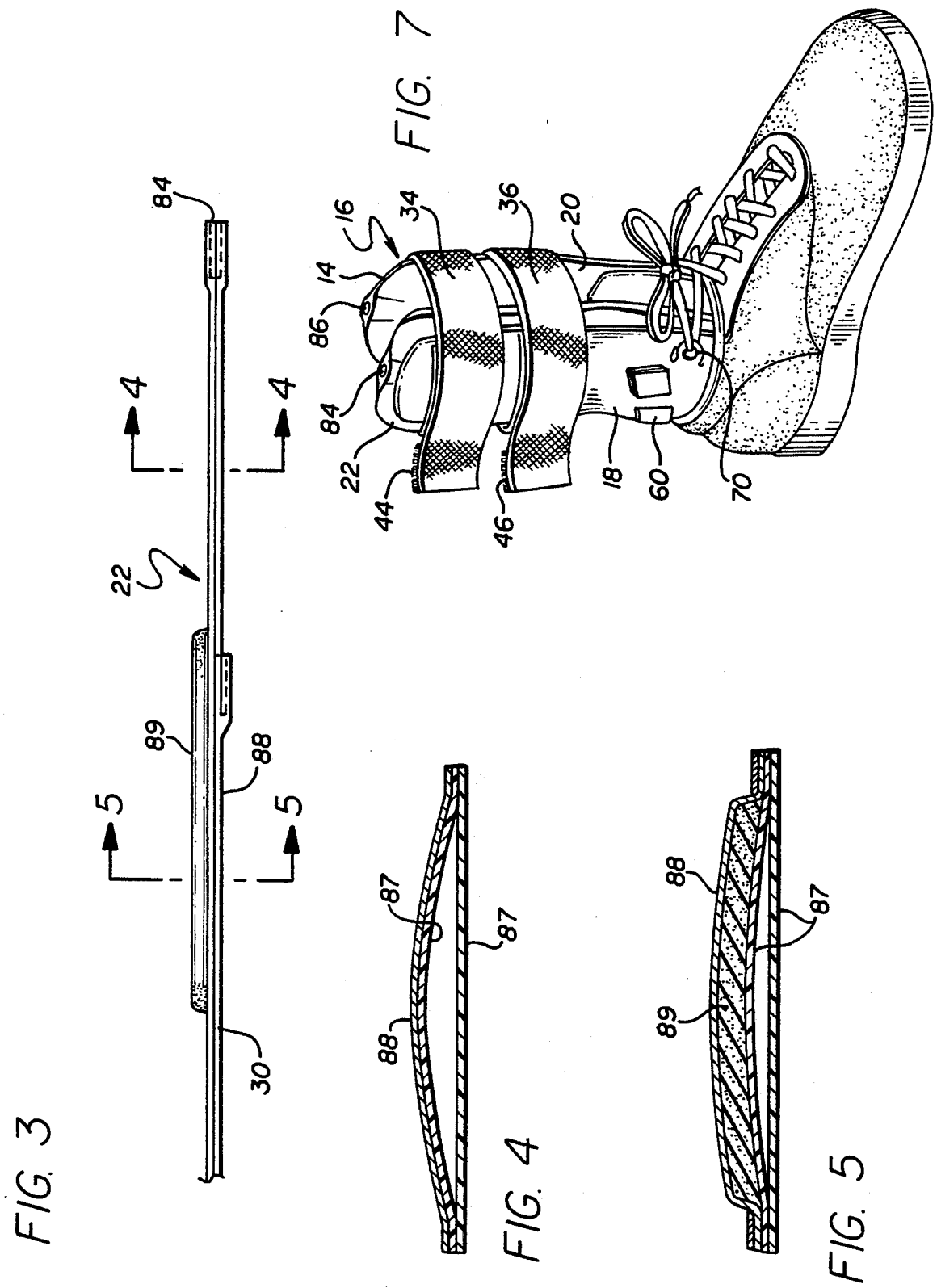

1

PNEUMATIC ANKLE BRACE WITH BLADDER AND PUMP ARRANGEMENT

FIELD OF THE INVENTION

The present invention relates to an improved orthotic or orthopaedic device, and specifically to an ankle brace for stabilizing an ankle before or after injury. In particular, the ankle brace of the present invention stabilizes the ankle against inversion and eversion and anterior subluxation while allowing normal dorsiflexion and plantarflexion movement and while further reducing swelling and increasing venous and lymphatic return in the lower leg extremity.

BACKGROUND OF THE INVENTION

After injury to an ankle, such as a fracture or severe sprain thereof, it is often necessary to completely immobilize the injured ankle through the use of a molded plaster or resin cast. Once the injury has been stabilized, however, recovery may be accelerated by removing the molded plaster or resin cast and replacing it with a removable functional walking brace so that the ankle can be exercised while healing.

Even if the injury is not severe enough to warrant complete immobilization of the ankle, it is still sometimes necessary to use a functional walking brace to stabilize the ankle against inversion (the foot rolling inward), eversion (the foot rolling outward) and/or anterior subluxation (partial dislocation) while still allowing the normal dorsiflexion and plantarflexion movements of the ankle.

A variety of ankle braces, walking casts and other orthopaedic ankle apparatuses have previously been proposed. For instance, in T. E. Grim, U.S. Pat. No. 4,977,891 ('891), an ankle brace comprising two relatively rigid side supports with inflatable bladders attached to them is described. The side supports are connected at their bottom by a flexible strap upon which is mounted an air pump. The air pump is activated by walking and running, and it causes the air bladders mounted on the side supports to inflate. The side supports are held firmly in place about the lower leg and ankle by straps. A relief valve and/or pin holes in the bladders prevent excessive pressure in the bladders and provide reduced support when the user is inactive. While this arrangement prevents undesired eversion, inversion and anterior subluxation caused by activity, it also allows for reduced pressure during rest periods.

Other ankle braces which have air inflatable bladders are shown in G. W. Johnson, Jr.'s U.S. Pat. Nos. 4,280,489 and 4,628,945. These prior art devices are intended to be worn within a separate shoe and are also inflatable with an external source of air pressure or they are preinflated.

Other arrangements have been proposed to promote healing of an injured foot, ankle and/or lower leg, as shown in C. G. Eischen, Sr., U.S. Pat. No. 4,805,601 in which the apparatus includes a bladder which completely encircles the ankle, connected by an opening to a bladder underlying the foot. In addition, various arrangements have been proposed for ventilating shoes by circulating air through the shoes. Typical patents showing this type of arrangement include M. Dunker, U.S. Pat. No. 2,552,711; D. W. Oltrogger, U.S. Pat. No. 2,560,591; A. C. Crawford, U.S. Pat. No. 2,676,422; C. N. Eaton, U.S. Pat. No. 3,029,530; E. Karras, U.S. Pat. No. 3,331,146; and J. Faiella, U.S. Pat. No. 4,414,760.

These patents disclose the use of air pumping arrangements actuated by foot pressure for circulating air through a shoe. Reference is also made to German publication designated Offenlegungsschrift No. 2321817, published Nov. 15, 1973, which publication shows a ski boot with inflatable ankle bladders, a rigid sole and a pump mounted in the sole. The pump can be latched to an inactive state when the inflatable pads are pressurized.

The prior art walking braces set forth above do not stabilize the ankle against anterior subluxation and permit plantarflexion and dorsiflexion while simultaneously increasing venous and lymphatic circulation and reducing swelling in the lower leg extremity by exercising the muscle groups of the lower leg. Thus, a principal object of the present invention is to effectively accomplish all of these functions.

SUMMARY OF THE INVENTION

In accordance with one specific illustrative embodiment of this invention, a new and improved pneumatic ankle brace is provided for insertion into a shoe having laces, which provides various and therapeutically desired amounts of pressure, support and massaging action to the foot, ankle and lower leg. The brace also has two inflatable, pulsating inflatable bladders. Additional non-pulsating air bladders may be formed in conjunction with a foot pump which may be interconnected to both the pulsating and non-pulsating air bladders. The inflatable bladders are attached to the inner portions of the side supports and may be distributed with a certain amount of preinflation. The foot pump is activated through normal use (walking, running, etc.) whereby an entrapped fluid, such as air, is displaced back and forth between two pulsating bladders. The foot pump thereby creates a pulsing action which leads to a massaging compression effect that will help reduce swelling and increase venous and lymphatic return. Additional inflatable bladders may be placed between the pulsating bladders and the foot, ankle, and lower leg to provide support and cushioning as well as protect the injured limb from the rigid support shell should any of the pulsating bladders puncture. Also included are the means for securing the bladder to the side supports and the entire brace to the ankle. These arrangements may include straps and D-rings, straps and Velcro-type fasteners, a counter strap extending between the side supports at a lower position just above the heel, and a fastener located on the side supports to receive the laces of the shoe to be tied or other appropriate systems.

The pump may be in the form of a relatively flat chamber underlying the heel of the user. It is essentially comprised of an open cell foam or a flexible hollow or curved resilient material, which when compressed, directs the entrapped fluid up into the bladders on both sides of the ankle. When foot pressure is released from the pump, its resilient configuration draws the fluid back into its volume. The pump may also include additional welded "darts" which will aid in reducing the thickness in certain areas of the pump to enhance comfort.

The pump is characterized by a variety of strategically placed weld lines which serve to create channels through which fluid transfer can take place.

The additional inflatable bladders may be located distally and adjacent to the pulsating bladders. They may also be made to pulsate or may serve as non-pulsating protecting membranes.

Accordingly, it is a primary object of the present invention to provide an improved pneumatic ankle brace whereby ankle support members are pressurized by an interconnected, preinflated foot pump which is activated through walking, running, and so forth by displacing the entrapped fluid in the pump between two or more bladders creating a pulsing action. This pulsing action creates a massaging compression effect that helps reduce swelling and increases venous and lymphatic return.

This pulsing action in the lower leg also helps prevent any significant atrophying of the lower leg muscles by facilitating blood and lymphatic fluid flow through the lower leg.

It is also an object of the present invention to prevent undesired inversion, eversion and anterior subluxation while allowing plantarflexion and dorsiflexion of the ankle.

Another object of this invention is to provide a more comfortable ankle brace which will firmly support an injured lower leg.

The foregoing and still further features and advantages of the present invention as well as a more complete understanding thereof will be made apparent from a study of the following detailed description of the invention in connection with the accompanying drawings.

BRIEF DESCRIPTION OF THE DRAWINGS

FIG. 3 is a partial side view of the bladder and pump arrangement taken along lines 3—3 of FIG. 2;

FIG. 4 is a cross-sectional view of one of the main bladders taken along lines 4—4 of FIG. 3;

FIG. 5 is a cross-sectional view of one of the additional bladders and cushioning member of the bladder taken along lines 5—5 of FIG. 3;

FIG. 7 is a perspective view of the ankle brace of FIG. 6 shown assembled and fitted and properly secured in a shoe having laces.

DETAILED DESCRIPTION OF PREFERRED EMBODIMENTS OF THE INVENTION

Figure 1:
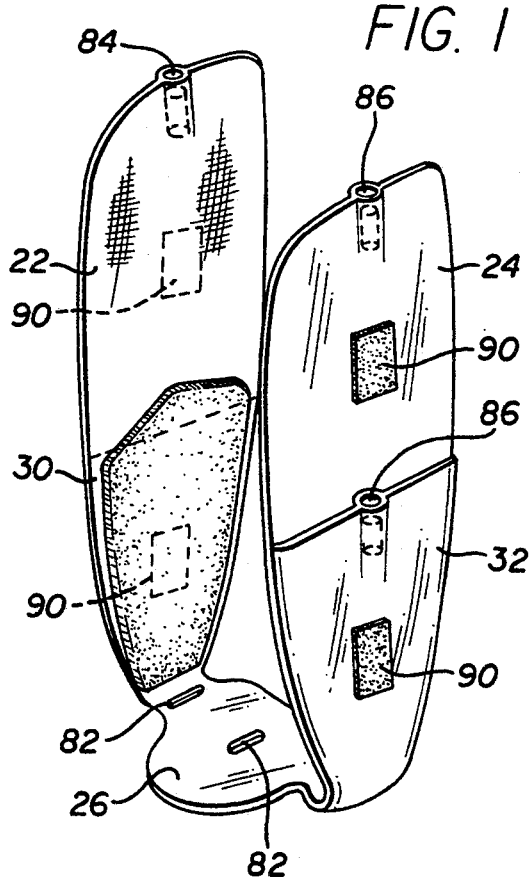
FIG. 1 is a diagrammatic, perspective view of a bladder and pump arrangement of the present invention.
Figure 2:
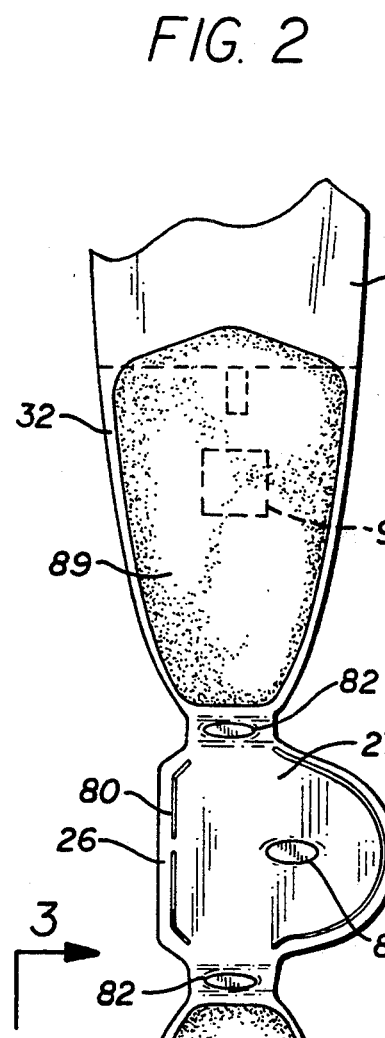
FIG. 2 is a partial, unfolded top plan view of the inside surface of the bladder and pump arrangement of FIG. 1.
Figure 8:
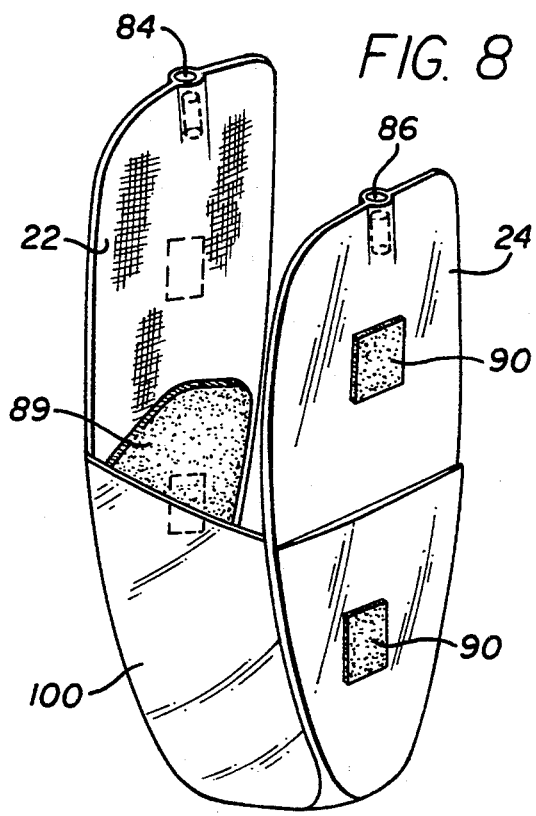
FIG. 8 is diagrammatic, perspective view of another embodiment of the bladder and pump arrangement of the present invention.
Figure 6:
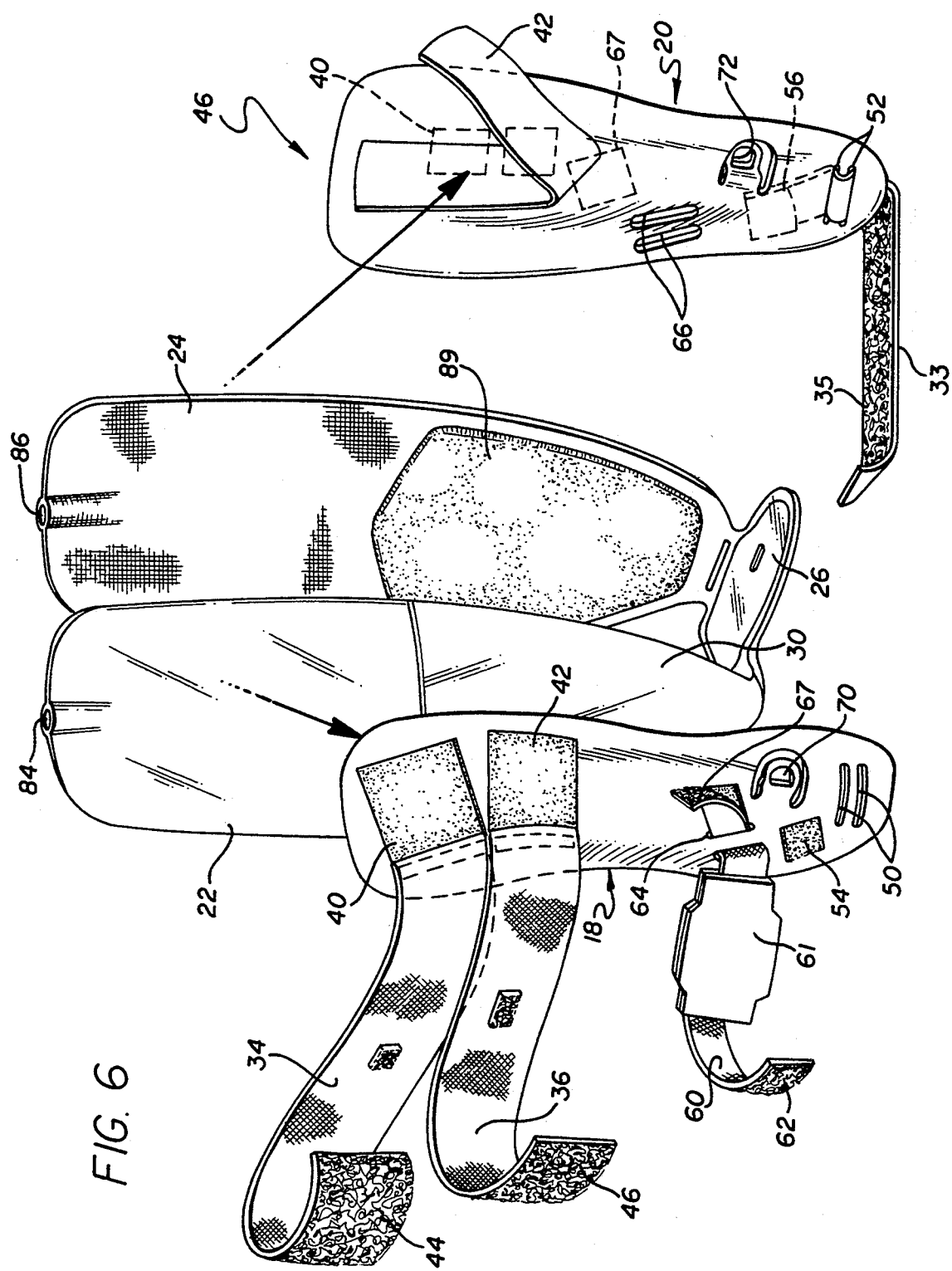
FIG. 6 is an exploded perspective view of the ankle brace of the present invention including the bladder and pump arrangement of FIG. 1.

With reference to FIGS. 6 and 7, the improved ankle brace 16 of the present invention includes a pair of side support members 18 and 20 preferably made of vacuum molded plastic, for example, nylon or rigid polypropylene, having sufficient thickness and other properties so that they are relatively stiff or rigid. They are shaped so as to fit about the lower leg and ankle and are approximately eight to ten inches long. Also included are two main inflatable bladders 22 and 24 and a pump 26 which are interconnected and in one embodiment are formed with one welding process. The inflatable bladders 22 and 24 can be attached to the side supports 18 and 20 using a Velcro-type fabric, double sided adhesive or any other suitable means. Additional inflatable bladders 30 and 32 as shown in FIGS. 1 and 2, placed distally upon the main inflatable bladders 22 and 24, are provided for in the present invention.

Interconnecting the two side support members 18 and 20 is a bottom strap 33. The bottom strap 33 may include a surface 35 of Velcro material and may be adjustable through the use of double openings 50 and 52 located near the bottom end of the side supports 18 and 20. The ends of the bottom strap 33 may be fixed in position with the use of additional Velcro material 54 and 56 located on the outside of the side support members 18 and 20. Specifically, the adjustment is accomplished by positioning the ends of the strap 33 to extend from the outside of each support member 18 and 20 through opening 50 or 52 and then through the other one of the openings 50 or 52 and then attached by the Velcro material 54. Thus, the proper distance may be easily adjusted between the side support members 18 and 20 at the lowermost portions thereof.

The side supports 18 and 20 may be securely attached around the lower leg and ankle just below the calf area using two strap members 34 and 36, as shown in FIGS. 6 and 7. These strap members 34 and 36 also include Velcro portions 40 and 42 on their outer surfaces, and with Velcro material 44 and 46 at the end portions of the straps. The Velcro portions 40 and 42 are attached to the side support 18 or 20. As shown in FIG. 7, these straps 34 and 36 may be tightly drawn around the lower leg using the Velcro material so that the ankle brace 16 securely and firmly supports the ankle.

The present invention includes, in addition to the strap arrangement set forth above, a counter strap 60 which is similar in construction to the bottom strap 33. Specifically, the counter strap 60 may include a cushioning pad 61 and an inner surface covered with Velcro material 62 and the strap may pass through double openings 64 in the side support 18 and double openings 66 in the other side support 20. An additional piece of Velcro material 67 is attached to side support member 18 and another piece of Velcro material 67 is attached to side support member 18 and another piece of Velcro material 67 is attached to side support member 20. By having this arrangement the counter strap 60 may be adjusted in a similar manner to the bottom strap 33 to prevent the back portion of the side support members 18 and 20 from twisting or flexing outward at the lower end of the ankle brace 16 to compress the distal ⅓ to ½ of the brace.

The present invention incorporates a lace fastening means similar to that set forth in detail in Grim, U.S. Pat. No. 4,844,094 to insure that the side supports 18 and 20 do not twist or flex outward and to more properly stabilize and compress the ankle against inversion, eversion and anterior subluxation. It is preferred, as shown in FIG. 7, that the lace fastening arrangement in the present invention comprises a hole or slot 70 and 72 integrally molded at the bottom end of each side support member 18 and 20. It is to be appreciated, however, that other attachment means such as those set forth in U.S. Pat. No. 4,844,094 may be used.

FIGS. 1 and 2 illustrate the inflatable bladder and pump arrangement of the present invention. The foot pump 26 is comprised of an open cell foam and/or a flexible hollow or curved resilient material (for example, rubber or plastic) which when compressed offers an increased pressurization of the entrapped fluid within its support membranes 27. The foot pump 26 is characterized by a variety of strategically placed weld lines 80, as shown in FIG. 2, which serve to create channels through which fluid transfer can take place between the pump 26 and the inflatable bladders 22 and 24. Other plastic construction techniques may be employed to create areas such as welded cavities 82 which aid in reducing the thickness in certain areas of the pump 26 to enhance comfort. The pump 26 may be constructed by welding in a foam of a thickness or space provided by the surrounding semi-enclosed pump material, preferably urethane or some other resilient material, whereby the foam is placed in a compressed state initially and when further compressed by the foot will be more resilient and recover quicker than if not compressed.

The foot pump 26 is approximately three and one-half inches in length and three inches in width.

In one embodiment of the present invention the two main inflatable bladders 22 and 24 are interconnected with the foot pump 26. In this embodiment, the two bladders 22 and 24 and the pump 26 are formed with one welding process and may be considered one member, but this invention is not so limited to not include those bladders which are connected to the pump by other fluid transfer means such as with tubes or valves.

As shown in FIGS. 1, 2, 3 and 8 the main bladders 22 and 24 each have inlet valves 84 and 86 which can be of a fairly flap-type valve. In such a valve, air drawn in (entering the bladders 22 and 24) forces the valve's sealing flaps, which are normally biased together, apart which allows the air to flow into the valve. Air forced in a direction opposite to the air drawn in (exiting the bladders 22 and 24) forces the flaps together which creates a substantially airtight seal. Other types of valve arrangements may be used such as an air pressure release and bleed valve or inlet valves.

Thus, as shown in FIG. 4, the main bladders 22 and 24 become inflated when air is directed through their valves 84 and 86. The bladders 22 and 24 expand a maximum width of approximately two and one-half inches. The preferred length of each main bladder 22 and 24 is approximately ten and one-half inches long and the width is approximately three and three-quarters inches. As also shown in FIG. 4, the walls 87 of bladder 22 and 24 are constructed of a non-porous resilient material such as urethane. Each wall 87 is approximately 0.015 inch thick and is capable of stretching under force to allow the bladders a variety of widths to accommodate a wider foot base. Further, a fabric coating 88, for example, Nylon-Lycra, may be attached to the plastic film that makes up the bladders 22 and 24 to allow the skin to breathe and to increase comfort to the user. This fabric coating 88 is approximately 0.002 inch thick in another embodiment of the present invention.

FIG. 5 shows a portion of the bladder that includes additional foam padding 89 which is located at the bottom half of each main bladder 22 and 24. This padding 89 is about five inches in length and provides further comfort to the region surrounding the ankle.

As shown in FIGS. 1, 2 and 3 two additional, smaller inflatable bladders 30 and 32 can be placed distally upon the main inflatable bladders 22 and 24 to provide cushioning and support as well as protect the injured limb from the rigid support shell should either main bladder 22 and 24 puncture. In another embodiment, additional bladders 30 and 32 may also be made to pulsate by activation of foot pump 26, and the longer main bladders 22 and 24 may serve as non-pulsating protective membranes. The smaller bladders 30 and 32 may be comprised of the same material and consist of the same valve arrangement as the main bladders 22 and 24.

The shorter additional bladders 30 and 32 extend from the bottom of the main bladders 22 and 24 to about halfway up towards the uppermost portions of the main bladders 22 and 24. The outside surfaces of each bladder 22, 30, 24 and 32 have a Velcro portion 90 attached to them in order to affix the support members 18 and 20 to the bladders. It should be further mentioned that all bladder arrangements 22, 30, 24 and 32, preferably, are to be distributed with a certain amount of preinflation.

The operation of the ankle brace 16 of the present invention would be as follows. The bladder and pump arrangement, as shown in FIG. 1 for example, is to be attached to the inside of the side supports 18 and 20. If the brace 16 has been previously used, the bottom strap 33 and the counter strap 60 would already have been adjusted. If not, the wearer would position the side supports 18 and 20 to both sides of the ankle, and then after the side supports 18 and 20 are properly positioned, the ankle brace 16 would be held in place using the strap members 34 and 36. The bottom strap 33 would then be adjusted by peeling the Velcro material 35 back from the corresponding Velcro material 54 and 56 and pulling up both sides of the strap 33 until the bottom of the side supports are firmly in position. The ends of the strap 35 would then be firmly pressed down on the Velcro material 54 and 56 to lock the strap 33 in position. Similarly the counter strap 60 would be adjusted to pull the back lower end of the side supports 18 and 20 together above the heel.

The shoe would now be fitted over the entire ankle brace 16, as shown in FIG. 7, and the laces laced through the holes 70 or in other fastening means located at the lower end of the side supports 18 and 20. The laces would then be pulled tightly and tied, again as shown in FIG. 7, so that the ankle brace 16 is firmly in position.

Subsequently the bladders 22, 30, 24 and 32 are inflated to their therapeutically desired pressure by using, for example, an attachable hand-held pump.

Therefore, while in use, the fluid within the pressurized ankle support bladders 22, 30, 24 and 32 and the interconnected preinflated foot pump is displaced back and forth between either the main bladders 22 and 24 and/or the shorter bladders 30 and 32 thereby creating a pulsing action which lends to a massaging compression effect that helps reduce swelling and atrophying and increases venous and lymphatic return throughout the lower leg while effectively preventing inversion, eversion and anterior subluxation of the ankle.

Although the invention has been described with reference to a particular embodiment, it is to be appreciated that other adaptations and modifications may be used without departing from the spirit and scope of the present invention. For example, in FIG. 8 a heel cup 100 which may or may not be inflatable may be included to provide further support to the ankle region. Also, a possible extra bladder surrounding the ankle may be incorporated into the brace 16 to contain gel, or to receive water, with or without foam, for hot or cold therapy. It is also noted that the two inflatable bladders may, if desired, be automatically inflated by the pump, which after a predetermined pressure is reached, shuts off its inlet, and provides the pulsing action to the inflatable bladders discussed above.

Accordingly, the present invention is not limited to the constructions precisely as shown in the drawings or described in the detailed description.

There has been described hereinabove an implementation of a novel ankle brace. Those skilled in the art may now make numerous uses of the present invention, including variations from the described embodiments without departing from the spirit of the invention which is defined solely by the scope of the following claims.

I claim:

1. A pneumatic ankle brace, comprising:
   first and second substantially rigid side supports configured for fitting about the lower leg of a user and for supporting both sides of the user's ankle;
   securing means for securing said side supports relative to the user to firmly encase the ankle; and
   a bladder-pump assembly including a first bladder, a second bladder, a resilient foot pump, first channel means for providing fluid communication back-and-forth between said first bladder and said foot pump, and second channel means for providing fluid communication back-and-forth between said second bladder and said foot pump, said first bladder being positioned to provide a cushion between one side of the ankle and said first side support, said second bladder being positioned to provide a cushion between the other side of the ankle and said second side support, said bladders at least in part supporting the user's foot and ankle against inversion and eversion, said bladder-pump assembly having a preinflated constant fluid volume during operation of said ankle brace, said foot pump being positioned under the foot and thereby subject to foot pressure during the user's foot impact activity;
   wherein said foot pump when subjected to repeated foot pressure and release thereof causes a pulsing action of fluid in said bladder-pump assembly back-and-forth between said first bladder and said pump through said first channel means and back-and-forth between said second bladder and said pump through said second channel means, the fluid pulsing action providing a massaging compression effect to the foot and the ankle to reduce swelling thereof.

2. The brace of claim 1 wherein said side supports are formed of a relatively stiff or rigid material and are limited to the sides of the lower leg, ankle, and heel of the user.

3. The brace of claim 1 further comprising one-way inlet valve means for supply fluid to said first and second bladders, and relief means for releasing fluid from said bladders over a predetermined period of time.

4. The brace of claim 1 further comprising lower ends of said side supports being insertable into sides of a shoe having laces, and fastening means on said side supports for receiving the laces of the shoe so that the laces can be tightened and tied to restrain movement of the ankle.

5. The brace of claim 1 further comprising additional bladders mounted distally upon said first and second bladders, said additional bladders having a certain amount of preinflation.

6. The brace of claim 1 further comprising a fabric laminated to said first and second bladders, adjacent to the lower leg extremity, to provide comfort to and to allow the skin of the user's lower leg extremity to breathe.

7. The brace of claim 1 wherein said foot pump is positionable under the user's heel and includes welded darts to reduce the thickness thereof in selected areas to increase the comfort of said ankle brace to the user.

8. The brace of claim 1 wherein said pump and said first and second bladders are formed as a single construction which includes integral means for regulating fluid flow between said pump and said bladders.

9. A method for immobilizing an ankle of an individual against inversion and eversion and to reduce swelling in the individual's lower leg extremity, said method comprising the steps of:
   securing a pair of substantially rigid side supports to encase the individual's ankle with a first bladder disposed between one side support and one ankle side and a second bladder disposed between the other side support and the other ankle side;
   positioning a resilient foot pump, which is in fluid communication with both the first and second bladders, underneath the individual's foot; and
   applying sequential pressure and at least partial release thereof to the resilient foot pump and through and by movement of the foot relative to a support surface;
   wherein said applying step moves fluid back-and-forth between the resilient foot pump and the first bladder and between the resilient foot pump and the second bladder, the fluid back-and-forth movements creating a pulsing action which has a massaging compression effect that reduces swelling of the individual's lower leg extremity.

10. The method of claim 9 further comprising placing cushioning and support bladders distally upon the first and second bladders.

11. The method of claim 9 wherein the bladders and the pump at least in part define a bladder-and-pump assembly, and during said applying step, the amount of fluid in the bladder-and-pump assembly remaining constant.

12. The method of claim 9 wherein said applying step includes the individual running or walking on that foot on the support surface.

13. The method of claim 9 further comprising, before said applying step, inserting the side supports, the first bladder, the second bladder and the foot pump, together with the individual's foot into a shoe which has laces, and thereafter, tightening the laces to restrain movement of the ankle.

14. The method of claim 13 wherein said inserting step includes (1) inserting lower ends of the side supports into the sides of the shoe, and said tightening step includes passing the laces through fasteners in the side supports.

15. The method of claim 9 further comprising supplying fluid to the bladders through at least one bladder inlet valve, and after said supplying step, releasing fluid from the bladders through at least one bladder relief valve.

16. The method of claim 9 wherein said pump positioning step includes positioning the resilient foot pump under the individual's heel, and wherein said fluid moving step includes increasing venous and lymphatic return in the individual's lower leg.

17. The method of claim 9 wherein said securing step includes (1) securely attaching the side supports around the lower leg and ankle just below the calf area using at least one length-adjustable strap and (2) extending a counter strap between the side supports and just above the individual's heel; wherein the side supports, bladders and foot pump together define an ankle brace; and further comprising lace fastening the ankle brace to and inside of a shoe.

18. The method of claim 9 wherein the bladders and the pump together define an assembly, and said securing step includes attaching the assembly to the side supports, the side supports and the assembly together defining an ankle brace, fitting the brace around the foot using adjustable straps, fitting a shoe having laces over the brace, using the shoe laces to fasten the ankle brace in position, and inflating the assembly to a desired pressure.

* * * * *